United States Patent [19]

Forlani et al.

[11] Patent Number: 5,214,018
[45] Date of Patent: May 25, 1993

[54] CATALYST PREPARED BY A PARTICULAR PREPARATION METHOD AND ITS USE IN A PROCESS FOR PREPARING TERTIARY OLEFINS FROM ALKYL-TERT-ALKYLETHERS

[75] Inventors: Orfeo Forlani, San Donato Milanese; Valerio Piccoli, Monza, both of Italy

[73] Assignee: Snamprogetti S.p.A., Milan, Italy

[21] Appl. No.: 911,712

[22] Filed: Jul. 10, 1992

[30] Foreign Application Priority Data

Jul. 18, 1991 [IT] Italy ................. MI91 A 001993

[51] Int. Cl.$^5$ .............................................. B01J 21/12
[52] U.S. Cl. .................................................. 502/263
[58] Field of Search ..................................... 502/263

[56] References Cited

U.S. PATENT DOCUMENTS

| | | | |
|---|---|---|---|
| 2,684,340 | 7/1954 | Baral et al. | 502/263 |
| 3,946,020 | 3/1976 | Minato et al. | 502/263 |
| 4,691,073 | 8/1987 | Michaelson | 585/639 |
| 4,988,659 | 1/1991 | Pecoraro | 502/263 |

FOREIGN PATENT DOCUMENTS

| | | |
|---|---|---|
| 0127959 | 12/1984 | European Pat. Off. . |
| 0184461 | 6/1988 | European Pat. Off. . |
| 8700166 | 1/1987 | PCT Int'l Appl. . |

*Primary Examiner*—Carl F. Dees
*Attorney, Agent, or Firm*—Oblon, Spivak, McClelland, Maier & Neustadt

[57] ABSTRACT

A catalyst for producing tertiary olefins from alkyl-tert-alkylethers is described, consisting of silica modified by adding alumina in a quantity of between 0.3 and 1% by weight with respect to the silica, and is prepared by a method consisting essentially of impregnating a silica with a solution of aluminium salts, followed by drying and calcining, the material then being subjected to purification treatment with aqueous acid solutions or with aqueous solutions which release acidity by thermal decomposition, followed by washing, a second drying and a second calcining.

5 Claims, No Drawings

CATALYST PREPARED BY A PARTICULAR PREPARATION METHOD AND ITS USE IN A PROCESS FOR PREPARING TERTIARY OLEFINS FROM ALKYL-TERT-ALKYLETHERS

This invention relates to a catalyst prepared by a particular method and its use in a process for producing tertiary olefins by decomposition of the corresponding alkyl-tert-alkylethers. Various methods for producing tertiary olefins are known. For example, some are based on the use of $H_2SO_4$, which however in addition to corrosion and pollution problems has various drawbacks, including the need to concentrate the acid before its recycling. Others are based on decomposition of the corresponding methyl ethers in the presence of suitable catalyst systems. However the use of known catalysts for this reaction leads in most cases to the formation of dialkylether following the dehydration of the corresponding primary alcohols.

This reaction proceeds more easily the higher the reaction temperature. Some of the known catalysts require the use of relatively high temperatures, resulting in a loss of alcohol with the consequent need to feed new alcohol to the initial etherification reaction.

In addition, this formation of dialkylether requires more complex plant because of the need to separate the dialkylether from the tertiary olefin. Again, the formation of a considerable quantity of dialkylether makes it necessary to dehydrate the primary alcohol before it is recycled, otherwise there would be phase separation during the etherification reaction, with the possible formation of tertiary alcohols.

A further drawback when the reaction is conducted beyond a certain temperature is the appearance of dimerization and trimerization of the tertiary olefin recovered from the ether decomposition. Some problems disappear if the tert-alkylether decomposition is conducted in the presence of a catalyst system consisting of activated alumina modified by partial substitution of the surface —OH groups by silanol groups as described in Italian patents Nos. 1001614 and 1017878 in the name of the present applicant. However the activated alumina modified as described in the aforesaid patents gives rise, even for a modest raising of the reaction temperature, to the formation of alkylether with consequent reduction in the recovery of primary alcohol for recycling.

In contrast, U.S. Pat. No. 4,254,296 of the present applicant uses a catalyst chosen from a crystalline silica modified with oxides of metal cations such as aluminium and boron, which gives much better performance than activated alumina modified with silanol groups.

However, this material has a very high production cost and is difficult to prepare.

In addition the siliconized alumina catalyst does not have a long life as it is unable to limit by-products to within limits which allow economically quantitative recovery of the products obtained. Higher dimethylether quantities correspond to higher methanol quantities and higher quantities of isobutene, which is lost during the distillation or separation stage.

European patent application EP-50992 of SUMITOMO Chem. Ind. claims a tertiary olefin production process using a catalyst prepared by high-temperature calcining of silica and an aluminium compound (particularly aluminium sulphate), in which the weight percentage of the aluminium compound is between 1 and 50% and preferably between 5 and 30%.

The present applicant has shown in European Patent No. 0 261 129—that using a catalyst consisting of silica modified by adding alumina in a quantity of between 0.1 and 1.5% by weight with respect to the silica, high conversion can be obtained provided that the silica used is of high purity.

The present applicant has now found that the conversion obtained with this type of catalyst can be substantially increased by a preparation method comprising purification treatment.

This substantial increase applies particularly to commercial silica, but even with high-purity silica the percentage conversion is a few points higher.

As demonstrated by the examples, it is important to effect the purification treatment downstream of the step involving silica impregnation with alumina if substantially higher results are to be obtained.

The catalyst according to the present invention for producing tertiary olefins from the corresponding alkyl-tert-alkylethers and consisting of silica modified by adding alumina in a quantity of between 0.3 and 1% by weight with respect to the silica is characterised by being prepared by a method consisting essentially of impregnating a silica with a solution of aluminium slats, followed by drying and calcining, the material then being subjected to purification treatment with aqueous acid solutions (such as HCl, $H_2SO_4$ etc.) or with aqueous solutions which release acidity by thermal decomposition, followed by washing, a second drying and a second calcining.

The preferred aqueous solutions which release acidity by decomposition are aqueous solutions of ammonium salts, in particular ammonium acetate, ammonium propionate and ammonium chloride.

The purification treatment is preferably conducted at a temperature of between 20° and 100° C. for a time of between 0.5 and 24 hours.

The aqueous solutions are preferably used at a molar concentration of between 0.05 and 0.5 in a quantity of between 1 and 20 times the volume of the material to be purified.

The present invention further provides a process for producing tertiary olefins consisting essentially of reacting the corresponding alkyl-tert-alkylethers in the presence of a catalyst obtained by the aforedescribed preparation method and consisting of silica modified by adding alumina in a quantity of between 0.3 and 1% by weight with respect to the silica.

In particular, said process can be used to obtain isobutene by decomposing methyl-tert-butyl-ether (MTBE).

The alkyl-tert-alkylether decomposition is conducted at a temperature equal to or lower than 500° C. and preferably between 130° and 350° C.

The operating pressure is generally between 1 and 10 $kg/cm^2$, and preferably at least equal to the vapour pressure of the recovered olefin at the condensation temperature used.

The space velocity expressed as liquid volume pre volume of catalyst per hour (LHSV) at which the reaction is conducted is between 0.5 and 200 $h^{-1}$ and preferably between 1 and 50 $h^{-1}$. The primary alcohols recoverable for the purpose of the decomposition process of the invention preferably contain from 1 to 6 carbon atoms.

The process of the present invention can be used to recover tertiary olefins from mixtures of $C_4$–$C_7$ olefins such as those originating from thermal cracking, steam cracking or catalytic cracking.

The various tertiary olefins obtainable in the pure state include isobutylene, isoamylenes such as 2-methyl-2-butene and 2-methyl-1-butene, isohexanes such as 2,3-dimethyl-1-butene, 2,3-dimethyl-2-butene, 2-methyl-1-pentene, 2-methyl-2-pentene, 3-methyl-2-pentene (cis and trans), 2-ethyl-1-butene, 1-methyl-cyclopentene, and tertiary isoheptenes.

The transformation of the tert-alkylether into primary alcohol and tertiary olefin is practically quantitative in accordance with the relative thermodynamic data.

The formation of very small quantities of dimers and trimers of the recovered tertiary olefin is noted, whereas there is no formation of tertiary alcohol.

The operation and the advantages of the process according to the present invention will be more apparent from an examination of the following illustrative examples, which are in no way to be considered as limitative of the invention.

EXAMPLES OF CATALYST PREPARATION

Example 1

The catalyst in the form of silica modified with alumina is prepared in the following manner:

10 g of commercial silica (980B of Shell), of composition:

| | |
|---|---|
| $Na_2O$ | 0.08 wt % |
| $SO_4$ | 0.10 wt % |
| $Al_2O_3$ | 0.10 wt % |
| $SiO_2$ | remainder to 100% | are impregnated with 8.5 cc of an aqueous solution containing 0.368 g of aluminium nitrate enneahydrate ($Al_2O_3$ added=0.5% by weight with respect to the silica); slow drying then follows at 120° C. for 3 hours, plus calcining at 500° C. for 4 hours. The material obtained is treated with 100 cc of an ammonium acetate solution (0.17 molar) at 50° C. for 2 hours.

The material is then separated from the solution and washed with deionized water (3 times with 100 cc), dried in an oven at 120° C. for 3 hours and calcined at 450° C. for 4 hours.)

Example 2

A catalyst is prepared in the manner of Example 1 starting from Shell 980B commercial silica.

Compared with Example 1, the 10 g of silica are impregnated with 8.5 cc of an aqueous solution containing 0.515 g of aluminium nitrate enneahydrate ($Al_2O_3$ added=0.7% by weight with respect to the silica).

Example 3

A catalyst is prepared in the manner of Example 1 starting from Shell 980B commercial silica.

Compared with Example 1, the 10 g of silica are impregnated with 8.5 cc of an aqueous solution containing 0.736 g of aluminium nitrate enneahydrate ($Al_2O_3$ added=1% by weight with respect to the silica).

Example 4 (Comparative)

A catalyst is prepared starting from 10 g of Shell 980B commercial silica.

The 10 g of silica are treated with 100 cc of an ammonium acetate solution (0.17 molar) at 50° C. for 2 hours.

The material is then separated from the solution and washed with deionized water (3 times with 100 cc), dried in an oven at 120° C. for 3 hours and calcined at 450° C. for 4 hours.

The material obtained is impregnated with 8.5 cc of an aqueous solution containing 0.736 g of aluminium nitrate enneahydrate ($Al_2O_3$ added=1% by weight with respect to the silica), slow drying then following at 120° C. for 3 hours, plus calcining at 500° C. for 4 hours.

Compared with Example 3, the purification treatment is conducted upstream of the impregnation with $Al_2O_3$.

Example 5-7 (Comparative)

Catalysts are prepared (Examples 5, 6 and 7) in a manner analogous to Examples 1, 2 and 3 respectively, but without conducting the purification treatment downstream of the first drying and first calcining steps.

EXAMPLES 8-10 (Comparative)

Catalysts are prepared (Examples 8, 9 and 10) in a manner analogous to Examples 5, 6 and 7 respectively but, instead of using the Shell 980B commercial silica, using a high purity AKZO silica of the following composition:

| | |
|---|---|
| $Na_2O$ | 0.02 wt % |
| $SO_4$ | 0.15 wt % |
| $Al_2O_3$ | 0.15 wt % |
| $SiO_2$ | remainder to 100% |

Examples of their use in the tertiary olefin production process

Examples 11-20

The catalysts prepared as described in Examples 1-10 are used in a process for producing tertiary olefins by methyl-tert-butylether (MTBE) decomposition.

The reaction conditions are as follows:

| | |
|---|---|
| Catalyst bed temperature | 130° C. |
| LHSV | 4 $h^{-1}$ |
| Inlet pressure | 1.4 ata |

The results obtained are given in Table 1, from which the beneficial effect of the catalyst purification treatment can be seen. The conversion is much higher than that obtained using catalysts prepared from commercial silica by known methods, and is also clearly higher than that obtained using catalysts prepared from high purity silica by known methods.

It can also be seen that when the purification treatment is conducted before the impregnation with $Al_2O_3$ the advantages are very modest (in terms not of conversion increase but rather of the conversion value obtained).

TABLE 1

| Example | % $Al_2O_3$ | % Na | Notes | Conversion |
|---|---|---|---|---|
| 11 | 0.5 | 0.08 | With purification treatment | 77 |
| 12 | 0.7 | 0.08 | " | 79 |
| 13 | 1.0 | 0.08 | " | 79 |
| 14 | 1.0 | 0.08 | With purification treatment upstream of impregnation | 55 |
| 15 | 0.5 | 0.08 | Without purification treatment | 29 |
| 16 | 0.7 | 0.08 | " | 35 |
| 17 | 1.0 | 0.08 | " | 38 |
| 18 | 0.5 | 0.02 | " | 64 |
| 19 | 0.7 | 0.02 | " | 69 |
| 20 | 1.0 | 0.02 | " | 69 |

We claim:

1. A catalyst for producing tertiary olefins from the corresponding alkyl-tert-alkylethers and consisting of silica modified by adding alumina in a quantity of between 0.3 and 1% by weight with respect to the silica, characterised by being prepared by a method consisting essentially of impregnating a silica with a solution of aluminium salts, followed by drying and calcining, the material then being subjected to purification treatment with aqueous acid solutions or with aqueous solutions which release acidity by thermal decomposition, followed by washing, a second drying and a second calcining.

2. A catalyst as claimed in claim 1, wherein the aqueous solutions which release acidity by thermal decomposition are aqueous solutions of ammonium salts.

3. A catalyst as claimed in claim 2, wherein the ammonium salts are chosen from ammonium acetate, ammonium propionate and ammonium chloride.

4. A catalyst as claimed in claim 1, wherein the purification treatment is conducted at a temperature of between 20° and 100° C. for a time of between 0.5 and 24 hours.

5. A catalyst as claimed in claim 1, wherein the aqueous solutions for the purification treatment are used at a molar concentration of between 0.05 and 0.5 in a quantity of between 1 and 20 times the volume of the material to be purified.

* * * * *